United States Patent [19]
Elliott et al.

[11] Patent Number: 6,135,114
[45] Date of Patent: Oct. 24, 2000

[54] VAGABOND RESTRAINT SYSTEM

[75] Inventors: Duane R. Elliott, 8202 N. Kenwood Ave., Indianapolis, Ind. 46260; Michelle Moscato, Indianapolis, Ind.

[73] Assignee: Duane R. Elliott, Indianapolis, Ind.

[21] Appl. No.: 09/038,235

[22] Filed: Mar. 11, 1998

[51] Int. Cl.[7] .................................................. A61B 19/00
[52] U.S. Cl. ........................ 128/869; 128/872; 128/876
[58] Field of Search ........................... 128/846, 869–876; 5/624, 625, 628

[56] References Cited

U.S. PATENT DOCUMENTS

| | | |
|---|---|---|
| 4,024,861 | 5/1977 | Vincent . |
| 4,506,664 | 3/1985 | Brault . |
| 4,601,075 | 7/1986 | Smith . |
| 4,736,474 | 4/1988 | Moran et al. . |
| 4,841,961 | 6/1989 | Burlage et al. . |
| 4,877,038 | 10/1989 | Fricke .................................... 128/876 |
| 4,970,739 | 11/1990 | Bradford . |
| 4,979,520 | 12/1990 | Boone, Jr. et al. . |
| 5,048,134 | 9/1991 | Dennill ................................... 128/870 |
| 5,048,541 | 9/1991 | Haneline . |
| 5,111,850 | 5/1992 | Kunofsky ............................... 128/869 |
| 5,263,214 | 11/1993 | McLaughlin et al. . |
| 5,435,323 | 7/1995 | Rudy . |
| 5,515,869 | 5/1996 | Powell et al. . |
| 5,560,059 | 10/1996 | McQueen ................................... 5/625 |

*Primary Examiner*—Michael A. Brown
*Attorney, Agent, or Firm*—Lowe Hauptman Gopstein Gilman & Berner

[57] ABSTRACT

A restraint system is disclosed for immobilizing injured patients and, more particularly, a releasable restraint using netting to restrain the patient. The patient restraint includes a pair of substantially parallel transverse straps and a pair of substantially parallel longitudinal straps connected between the transverse straps. A net is interconnected between the transverse straps and the longitudinal straps along the periphery of the net. Each transverse strap includes two releasable fastener assemblies with one releasable fastener assembly being connected to either end portion of the strap. The releasable fastener assemblies include a first connector attached to the transverse strap at a position adjacent to where the longitudinal strap is connected to the transverse strap, and a mating second connector attached to a terminal end of the transverse strap. A second embodiment of the patient restraint further includes a pair of releasable padded shoulder straps connected between the transverse straps. The patient restraint may be used in combination with a wide variety of supporting structures.

25 Claims, 3 Drawing Sheets

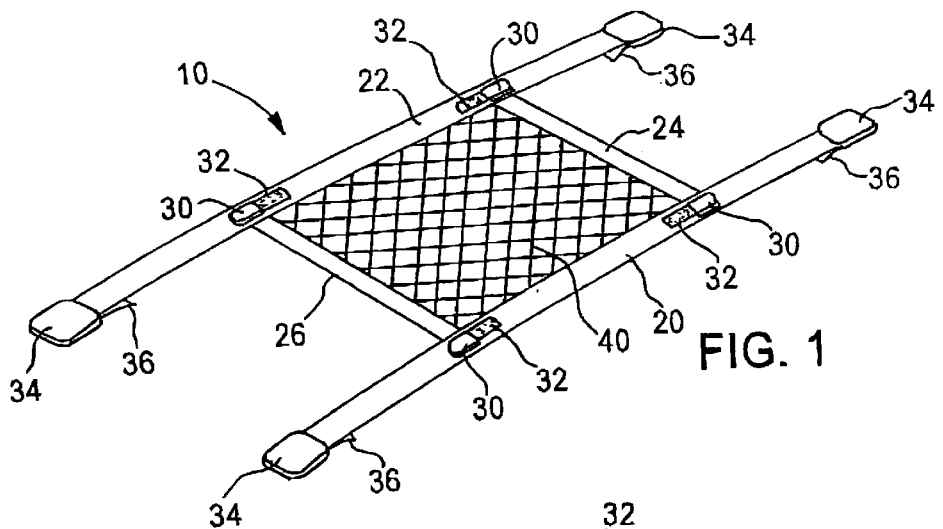
FIG. 1
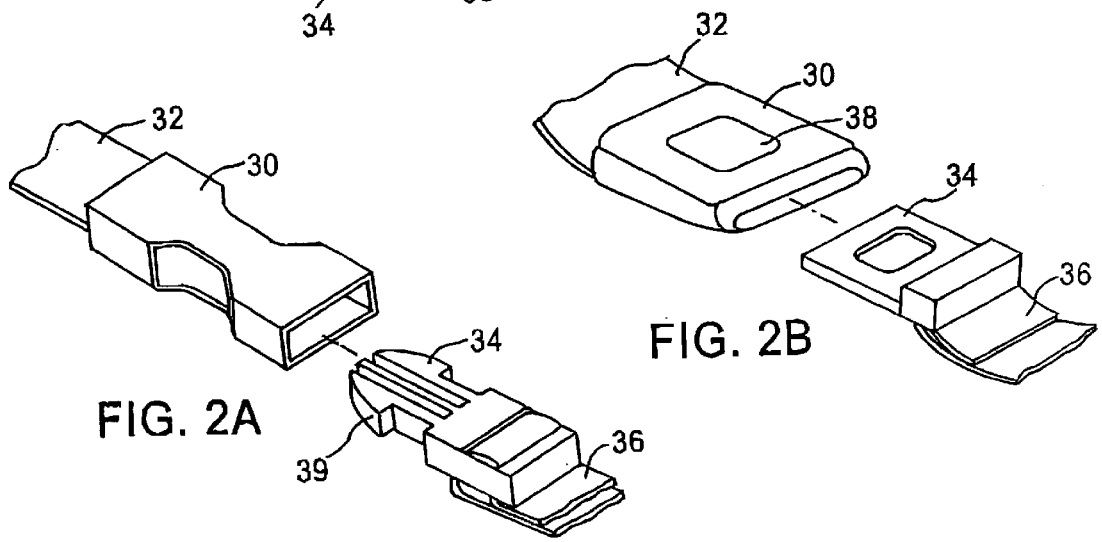
FIG. 2A
FIG. 2B
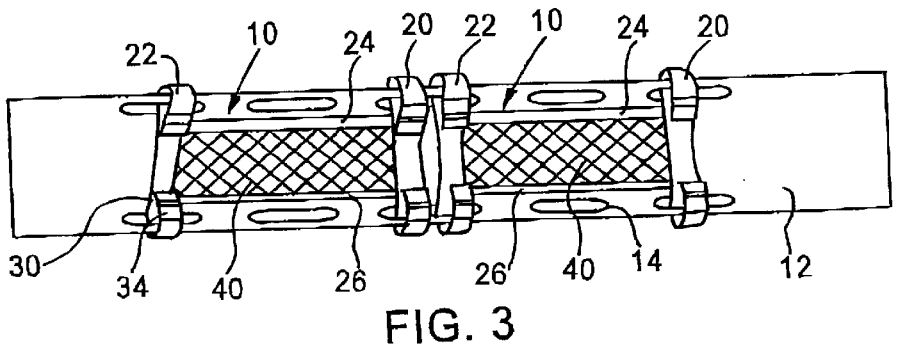
FIG. 3

VAGABOND RESTRAINT SYSTEM

TECHNICAL FIELD

The present invention relates generally to restraint systems for immobilizing injured patients and, more particularly, to a quick release restraint using netting to restrain the patient.

BACKGROUND ART

Time is of the essence when transporting an injured person from an accident scene to the hospital (or from hospital to hospital). Delays in receiving medical treatment at the hospital can sometimes have dire consequences. An injured person may inadvertently cause further injury to themself if not immobilized during transport to the hospital. Consequently, a need exists for a patient restraint that quickly and securely immobilizes an injured person during transportation from an accident scene as well as in other circumstances where an injured person must be transported.

Many devices have been developed to secure an injured person to a supporting structure during transportation from an accident scene to a hospital. Unfortunately, however, many of the restraint devices and supporting structures that have been developed are awkward and unwieldy to use at the oftentimes cramped environment of an accident scene. Typically, these devices employ a large number of straps and fasteners in order to properly secure the patient during transportation. The large number of straps and fasteners slow down the response time of emergency personnel because the straps and fasteners have a tendency to become tangled, or caught under the body of the injured person or under the supporting structure. Many patient restraint devices are also constructed with straps and fasteners that are fixed to the supporting structure. If, however, the restraint device is detachably connected to the supporting structure then the restraint device can be removed from the structure prior to positioning the injured person on the structure to avoid any entanglement. The ideal patient restraint device and supporting structure are constructed so that emergency personnel can quickly manipulate the injured person, the restraining device, and the supporting structure in any environment.

Additionally, many devices restrict the ability of emergency personnel to administer medical attention due to their almost complete encapsulation of the injured person. The ideal patient restraint device is constructed so that emergency personnel can visually inspect wounds and administer medical attention to the injured person during transportation while maintaining the injured person in an immobilized state.

An example of a patient restraint device is described in U.S. Pat. No. 4,970,739, issued on Nov. 20, 1990, to Bradford for a stretcher used to transport a patient in an immobilized condition. The stretcher described in the '739 patent includes a body supporting member within a frame and elongated flaps connected to the frame which define a tapered body support zone for immobilizing the patient. The elongated flaps are connected to the frame and thereby are difficult to manipulate in the cramped accident environment and have the potential of getting into the way of emergency personnel while the injured person is being immobilized. Any delay in receiving medical attention caused by the construction of the patient restraining device can be life threatening to a seriously injured person. Additionally, the elongated flaps of the restraint device of the '739 patent covers the body of the injured person from the neck to the knees and prevents emergency personnel from administering medical attention to those areas during transportation.

One example of a patient restraint which is simple in construction and easy to manipulate and use to secure a patient is described in U.S. Pat. No. 5,048,541, issued on Sep. 17, 1991, to Haneline. The restraining device described in '541 is used for restraining the patient against a substantially vertical film backboard of an upright X-ray station. The restraining device includes a pair of brackets mounted to the backboard, a restraint strap, fasteners for engaging the strap to the brackets, and at least one genital shield. The patient restraint described in '541 is specifically designed to position a person during an X-ray session and is insufficient to properly secure an injured person to a supporting structure. The patient restraint of the '541 patent does not provide sufficient immobilization of the shoulders, torso, and legs of the person for transportation. The expanded central portion of the strap prevents the emergency personnel from administering medical attention to the areas covered by the expanded central portion during transportation.

DISCLOSURE OF THE INVENTION

It is, therefore, an object of the present invention to provide a patient restraint that substantially eliminates the above-mentioned problems and substantially fulfills the above-mentioned needs.

It is an object of the present invention to provide a patient restraint device that is constructed so that emergency personnel can quickly manipulate the injured person, the restraining device, and the supporting structure in any environment.

It is another object of the present invention to provide a patient restraint device constructed to be removably attached to almost any patient supporting structure.

A further object of the present invention is to provide a patient restraint device constructed so that emergency personnel can administer medical attention to the injured person during transportation while maintaining the injured person in an immobilized state.

Another object of the present invention is to provide a patient restraint that is cost effective to manufacture, easy to use, and reliable in operation.

These and other objects of the present invention are achieved by a patient restraint that is constructed to include a pair of transverse straps having a net connected therebetween, and at least one releasable fastener assembly attached to each transverse strap. The releasable fastener assemblies are simple and effective mechanisms for detachably connecting the patient restraint to a supporting structure such as a stretcher. The construction of the present invention, specifically the pair of transverse straps having a net connected therebetween, ensures that the injured person is immobilized during transport due to the broad coverage it provides over the body of the injured person. Additionally, the net not only immobilizes the injured person, but also the open lattice network that constitute the net allow emergency personnel to visually inspect wounds and administer shots or other medical attention therethrough. The patient restraint preferably includes a pair of longitudinal straps connected between the pair of transverse straps with the net being interconnected between the longitudinal straps and the transverse straps.

A second embodiment of the patient restraint further includes a pair of shoulder straps that have a fixed end connected to one of the transverse straps and a free end releasably fastened to the other transverse strap. The pair of shoulder straps can be wrapped around the infant thereby securing the infant to the restraint and then the restraint is attached to the supporting structure. The second embodiment is particularly well suited for use with infants because the shoulder straps can be loosely wrapped around the infant to secure the infant without the need for tightening the transverse straps or the netting so that they are uncomfortably tight on the infant. Preferably, a patient restraint of the present invention constructed to be used with an infant includes padding on both shoulder straps and both transverse straps.

Another object of the present invention is to provide a patient restraint assembly including a patient restraint device and supporting structure constructed so that emergency personnel can quickly manipulate the injured person, the restraining device, and the supporting structure in any environment.

According to yet another object of the invention, a patient restraint assembly including a patient restraint device and supporting structure is provided that are cost effective to manufacture, easy to use, and reliable in operation.

These and other objects of the present invention are achieved by combining a patient restraint as set forth above with a supporting structure including a transport member and a riser portion. The transport member has a generally rectangular shape and a plurality of apertures arranged in two parallel rows extending along two opposing edges thereof that are used for securing the patient restraint device to the supporting structure. The supporting structure is made of plastic because, even when dented and nicked during use, plastic can be easily washed and sanitized after use without the risk of harboring germs. The riser portion allows hospital workers to slide their fingers under the edge of the transport member and lift the supporting structure off of a surface. The riser portion also allows workers to easily secure the patient restraint device to the supporting structure by giving the workers clearance to thread the releasable fastener assemblies through the apertures in the supporting structure.

Alternatively, these and other objects of the present invention are achieved by combining a patient restraint as set forth above with a transport cradle having a transparent plastic cradle shell with cushioning lining the interior surface of the cradle shell. The cradle is made of plastic because, even when dented and nicked during use, plastic can be easily washed and sanitized after use without the risk of harboring germs. The patient restraint may be quickly and easily secured to the cradle by extending the transverse straps and releasable fastener assemblies through apertures in the sides of the cradle shell. Alternatively, the patient restraint and transport cradle can be quickly and easily secured to an isolet by extending the transverse straps and releasable fastener assemblies through apertures in the sides of the cradle shell and then through the apertures in the isolet.

Still other objects and advantages of the present invention will become readily apparent to those skilled in this art from the following detailed description wherein only the preferred embodiments of the invention are shown and described, simply by way of illustration of the best mode contemplated of carrying out the invention. As will be realized, the invention is capable of other and different embodiments, and several details are capable of modifications in various obvious respects, all without departing from the invention. Accordingly, the drawings and description are to be regarded as illustrative in nature, and not as restrictive.

BRIEF DESCRIPTION OF DRAWINGS

For a more complete understanding of the present invention and advantages thereof, reference is now made to the following description taken in conjunction with the accompanying drawings in which like reference numbers indicate like features and wherein:

FIG. 1 is a perspective view of a first embodiment of a patient restraint according to the present invention;

FIG. 2A is an enlarged, exploded, perspective view of a releasable buckle according to the present invention;

FIG. 2B is an enlarged, exploded, perspective view of a side release fastener according to the present invention;

FIG. 3 is a top plan view of a pair of patient restraints according to the first embodiment of the present invention as used with a stretcher;

BEST MODE FOR CARRYING OUT THE INVENTION

Figure 4:
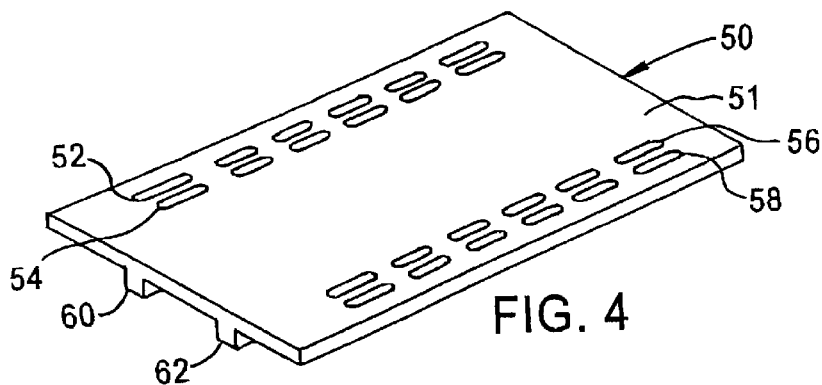
FIG. 4 is a perspective view of a supporting structure including a transport member and a riser portion according to the present invention.

Refer now to FIG. 1 where a first embodiment of the inventive patient restraint, generally indicated at 10, is illustrated in a flat unconnected position.

A first embodiment of the patient restraint 10, as depicted in FIG. 1, includes a pair of substantially parallel transverse straps, or first and second elongated members, 20 and 22. The patient restraint 10 preferably includes a pair of substantially parallel longitudinal straps, or third and fourth elongated members, 24 and 26, connected between the transverse straps, 20 and 22. A net 40 is interconnected between the transverse straps, 20 and 22, and the longitudinal straps, 24 and 26. Each transverse strap, 20 and 22, preferably includes two releasable fastener assemblies with one releasable fastener assembly being connected to either end portion of the transverse straps. Each releasable fastener assembly includes a first connector 30 and a second connector 34. The longitudinal straps, 24 and 26, are not essential to the construction of a working embodiment and, therefore, one or both may be eliminated from the construction if so desired.

The distance between the longitudinal straps, 24 and 26, is preferably smaller than the width of the average stretcher or gurney so that the longitudinal straps, 24 and 26, do not interfere with the attachment of the releasable fastener assemblies to apertures in the stretcher, as will be more fully discussed below. The distance between the transverse straps, 20 and 22, can be varied depending on the intended use of the patient restraint 10. For example, the distance between the transverse straps, 20 and 22, can be made to equal the distance from the neck area to the ankle or foot area of an average size adult, if the patient restraint 10 is intended to be used to immobilize adults. Similarly, the distance between the transverse straps, 20 and 22, can be made to equal the distance from the neck area to the ankle or foot area of an average size infant or child, if the patient restraint 10 is intended to be used to immobilize infants or children. Note that a universally sized patient restraint 10 can be produced where the distance between the transverse straps, 20 and 22, is, for example, two feet. Such a universally sized patient restraint 10 can be used in conjunction other patient restraints 10 to achieve a desired immobilization result, as will be more fully discussed below with reference to FIG. 3.

The terminal ends of the longitudinal straps, 24 and 26, are sewn to the transverse straps, 20 and 22, at position inward from the terminal ends of the transverse straps, 20 and 22. Preferably, the periphery of the netting 40 is sewn to the straps, 20, 22, 24, and 26. Other conventional fastening methods may alternatively be used if so desired. The netting 40, the straps, 20, 22, 24, and 26, and all of the interconnections therebetween should be made strong enough to safely hold the weight of even the largest of individuals. The netting 40, the straps, 20, 22, 24, and 26, and all of the interconnections therebetween should also be made strong enough to withstand an accident, such as an accidental dropping of the stretcher 12 and patient.

The transverse straps, 20 and 22, and the longitudinal straps, 24 and 26, are preferably constructed of webbing identical to that used to manufacture automobile seat belts, although other similar material may alternatively be used. The straps, 20, 22, 24, and 26, are preferably made from substantially inextensible nylon webbing having an average breaking strength of three thousand pounds or greater. The netting 40 may be constructed of a variety of materials that range from being substantially inelastic to materials that are elastic, e.g. double in length under a ten pound load. If a tight restraint is desired to hold the patient firmly in position, then the manufacturer can use a netting 40 which is made from a substantially inelastic material. If a soft restraint is desired then the netting 40 can be made from an elastic material. Preferably, the netting 40 is made of nylon and constitutes an open lattice network. One benefit of using netting 40 over a solid piece of fabric is that it allows the emergency personnel to visually inspect the patient's wounds and administer medical attention to the injured person through the netting 40 during transportation while maintaining the injured person in an immobilized state.

The releasable fastener assemblies include first connectors 30 attached to the transverse straps, 20 and 22, at a position adjacent to where the longitudinal straps, 24 and 26, are connected to the transverse straps, 20 and 22. The releasable fastener assemblies also include second connectors 34 attached to the terminal ends of the transverse straps, 20 and 22. The first connectors 30 are adapted to releasably mate with the second connectors 34.

In the preferred embodiment the first connectors 30 are female connectors which are attached to straps 32 that are sewn to the transverse straps, 20 and 22, at a position adjacent to where the longitudinal straps, 24 and 26, are connected to the transverse straps, 20 and 22. In the preferred embodiment the second connectors 34 are male connectors which are adjustably attached to the terminal ends of the transverse straps, 20 and 22. As is apparent to one skilled in the art, the first connectors 30 can alternatively be male connectors and the second connectors 34 can alternatively be female connectors. Also in the alternative, the first connector 30 can be adjustably attached to strap 32.

The adjustable end portion 36 of the transverse straps, 20 and 22, allows the emergency personnel or hospital workers to adjust the effective lengths of the transverse straps, 20 and 22, thereby tightening or loosening the patient restraint 10 against the body of the patient. The second connector 34 preferably has a conventional mechanism (typically a frictional locking mechanism) for holding the adjustable end portion 36 in a fixed position when it is tightened, thereby preventing the patient restraint 10 from becoming loose on the patient.

The releasable fastener assemblies may be side release fasteners as depicted in FIG. 2A, or releasable buckles identical in construction to automobile seatbelt buckles as depicted in FIG. 2B, or some other similar releasable fastener assembly. Preferably, the releasable fastener assemblies are constructed to prevent accidental unlatching of the fastener when brushing against or bumping into an obstacle. For this reason, hook and loop fasteners and conventional airplane style seatbelt buckles having a release lever (sometimes referred to as a cam buckle) are preferably not used, except in certain circumstances where other precautions are taken as discussed below.

The side release fastener assembly depicted in FIG. 2A is one example of a simple yet effective conventional releasable fastener assembly that can be used as part of the patient restraint 10 of the present invention. The side release fastener assembly has a female first connector 30 and a male second connector 34, both of which are conventionally made of a plastic material. The side release fastener assembly has a pair of opposing release buttons 29 on the male connector which when pinched towards one another release the second connector 34 from the first connector 30.

The releasable automobile seatbelt buckles depicted in FIG. 2B are a second example of a simple yet effective conventional releasable fastener assembly that can be used as part of the patient restraint 10 of the present invention. The releasable automobile seatbelt buckle has a female first connector 30 and a male second connector 34. The releasable automobile seatbelt buckle has a release button 38 which when depressed releases the second connector 34 from the first connector 30.

As is apparent to one skilled in the art, numerous types of releasable fastener assemblies may alternatively be used. The two examples depicted in FIGS. 2A and 2B are merely given by way of illustration and not limitation. Generally speaking other buckles that release by pressing a release button are acceptable for the purposes herein described. Additionally, numerous other types of release fasteners are acceptable as long as they are not readily susceptible to accidental release when the fastener assembly is brushed against or bumped into an obstacle.

The patient restraint 10 of the present invention is versatile in that it can be attached to a variety of different supporting structures in order to secure a patient. For example, FIG. 3 depicts two patient restraints 10 side by side each in a restraining position attached to a stretcher 12. The patient restraints 10 are attached to the stretcher 12 by extending the second connectors 34 downward through one of the apertures 14 in the stretcher 12 and then upward around the edge of the stretcher. The second connectors 34 are then fastened to the first connectors 30, thereby fastening the patient restraint 10 to the stretcher 12. Then the adjustable end portions 36 of the transverse straps, 20 and 22, are pulled to tighten the patient restraint 10 snug against the patient. Note that to release the patient from the stretcher 12 only the releasable fastener assemblies on one side of the stretcher 12 need to be released and the releasable fastener assemblies still connected on the opposing side of the stretcher 12 act as a hinge.

A single patient restraint 10 may be used to transport a child on a stretcher 12. In addition, the patient restraint 10 may be used in conjunction with other patient restraints 10, as depicted in FIG. 3, in order to give the proper support for the patient. Alternatively, the dimensions of the longitudinal straps, 24 and 26, and the netting 40 can be varied such that one patient restraint could extend the length of the stretcher 12, or at least extend from the neck area to the ankles of an average size adult. If the length of the longitudinal straps, 24 and 26, are increased it may be necessary to add extra transverse straps with releasable fastener assemblies in a substantially parallel relationship to and between the existing transverse straps, 20 and 22, in order to properly secure the patient upon the stretcher 12.

If the stretcher, or other transport device, does not have apertures for securing the patient restraint 10, then the second connectors 34 may be looped under the stretcher 12 and attached to either first connector 30 on its respective transverse strap. Note that if the patient restraint is constructed for such a use, then only one releasable fastener assembly, i.e. one first connector 30 and one second connector 34, is needed for each transverse strap, 20 and 22. If the patient restraint 10 is intended for such a use it will need to be manufactured with transverse straps, 20 and 22, of sufficient length in order to wrap around the stretcher or other supporting structure. The transverse straps, 20 and 22, will need to be nearly twice as long as otherwise necessary in order to wrap around the supporting structure.

The patient restraint 10 of the present invention may be used on a variety of supporting structures in order to secure a patient. In addition to being used on any style stretcher, the patient restraint can be used on other supporting structures such as hospital beds, wheelchairs, gurneys, operating tables, or any other supporting structures. For example, the transverse straps, 20 and 22, of the patient restraint 10 may be wrapped around the lower side railings on a conventional hospital bed and fastened using the releasable fastener assemblies, thereby preventing the patient from falling from the bed and causing further injury. Also, the transverse straps, 20 and 22, of the patient restraint 10 may be wrapped around the side back support posts of a wheelchair and fastened using the releasable fastener assemblies. Alternatively, the second connectors 34 may be looped around the back support of the wheelchair and attached to either first connector 30 on its respective transverse strap, as described above for the stretcher 12. These examples are merely illustrative of the wide variety of potential applications of the patient restraint 10 of the present invention.

Figure 5:
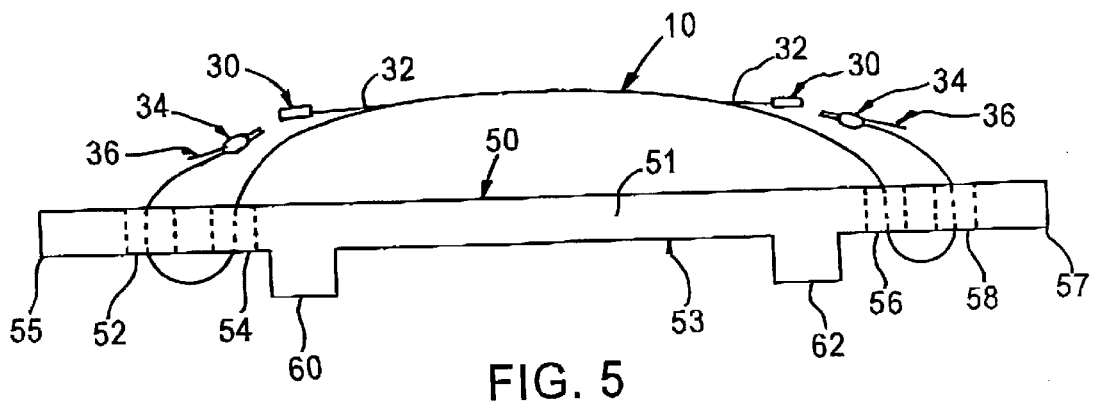
FIG. 5 is a side view of a restraint assembly including a supporting structure and patient restraint according to the present invention depicting the interconnection between the restraint and the supporting structure.

Referring now to FIGS. 4 and 5, the present invention further includes the combination of a patient restraint 10 as set forth above with a plastic supporting structure 50. The supporting structure 50 includes a transport member 51 of a generally rectangular shape, although other shapes may alternatively be used. The supporting structure has a plurality of apertures extending along two opposing edges thereof. Preferably, the supporting structure 50 has two rows of six apertures, 52 and 54, in the shape of elongated slots along one edge of the supporting structure 50, and two rows of six apertures, 56 and 58, in the shape of elongated slots along an opposite edge of the supporting structure 50.

As depicted in FIG. 5, the patient restraint 10 is attached to the supporting structure 50 by extending the second connectors 34 downward through one of the apertures in rows 54 and 56, and then upward through the adjacent apertures in rows 52 and 58, respectively. The second connectors 34 are then fastened to the first connectors 30, thereby fastening the patient restraint 10 and the patient to the supporting structure 50.

The supporting structure 50 preferably includes a riser portion attached to a bottom surface 53 of the transport member 51. The riser portion in the preferred embodiment includes a first riser 60 and a second riser 62. Each riser is preferably rectangular in cross-section and extends the length of the supporting structure 50. The risers, 60 and 62 are positioned on the inside of the apertures, 54 and 56 respectively, as depicted in FIGS. 4 and 5. Alternatively, the riser section could be constructed of a single riser (not shown) of sufficient width, for example a width equal to ¾ of the overall width of the transport member 51, to give the supporting structure 50 stability when it is resting on a surface. These examples are merely illustrative of the wide variety of potential configurations for the riser section as contemplated by the present invention in the goals as set forth above.

The riser portion allows hospital workers to slide their fingers under the side edges, 55 and 57, of the transport member 51 and lift the supporting structure 50 off of a surface. The riser portion also allows the hospital workers and emergency personnel to extend the second connectors 34 of transverse straps, 20 and 22, downward through the apertures, 54 and 56, and upward through the apertures, 52 and 58, without interference from the surface the supporting structure 50 is resting upon.

The supporting structure 50 is preferably manufactured using a material that is easy to clean and maintain, such as plastic. Even when dented and nicked during use, plastic can be easily washed and sanitized after use without the risk of harboring germs.

Figure 6B:
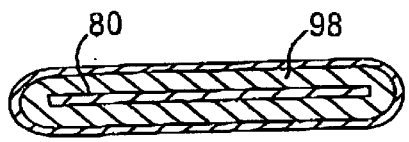
FIG. 6B is a cross-sectional view of a shoulder strap according to the second embodiment of a patient restraint of the present invention.
Figure 6A:
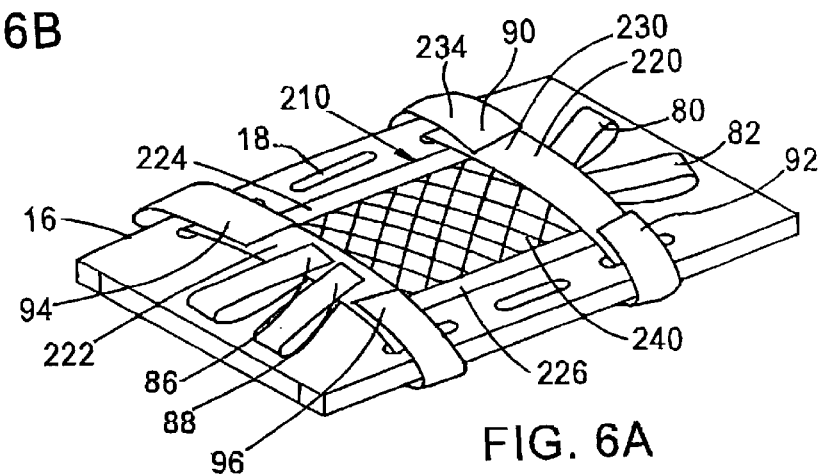
FIG. 6A is a perspective view of a second embodiment of a patient restraint according to the present invention.

Referring now to FIGS. 6A and 6B, a second embodiment of the patient restraint 210 is depicted in a restraining position attached to an isolet 16 typically used in neonatal care. The second embodiment of the patient restraint is particularly well suited for transporting an infant. The second embodiment of the patient restraint 210 is similar to the first embodiment described above except for three special features hereinafter discussed. First, the second embodiment further includes a pair of shoulder straps, or fifth and sixth elongated members, 80 and 82. Second, as depicted in FIG. 6B, the second embodiment preferably includes padding 98 on both shoulder straps, 80 and 82, and both transverse straps, 220 and 222. The releasable fastener assemblies, 90, 92, 94, and 96, of the second embodiment are preferably hook and loop fasteners.

The shoulder straps, 80 and 82, each have a fixed end connected to the transverse straps 220 at a position near the midpoint thereof, and a free end releasably fastened to the other transverse strap 222 at a position near the midpoint thereof. Preferably, the infant is laid down on a flat surface and the second embodiment of the patient restraint 210 is laid on top of the infant. The patient restraint is positioned on the infant with the head of the infant being outside of the netting 240 and above transverse strap 222 and the feet of the infant adjacent transverse strap 220. The shoulder straps, 80 and 82, are then extended in between the baby's legs and positioned in the crotch area of the baby. The shoulder straps, 80 and 82, are then extended under the body of the infant, and over the infant's shoulders on either side of the infant's head. The shoulder straps, 80 and 82, are then fastened to transverse strap 222 at a position near the midpoint thereof.

The second embodiment of the patient restraint 210 of the present invention preferably includes padding 98 on both shoulder straps, 80 and 82, and both transverse straps, 220 and 222. The padding 98 may also be used on the longitudinal straps, 224 and 226. The padding 98 is constructed to protect the delicate skin of a newborn child from irritation due to contact with the patient restraint 210. Preferably the padding is made from 100% nylon fabric sewn to the straps with 100% polyester foam filler therein. Note that the first embodiment of the present invention may also be manufactured with such padding if it is desired to use the first embodiment on infants. The padding 98 may either be wrapped around the exterior of the straps, as depicted in FIG. 6B, or attached to the interior surfaces of the straps which are likely to come into contact with the infant or any combination thereof.

The releasable fastener assemblies, 86 and 88, for the shoulder straps, 80 and 82, of the second embodiment are preferably hook and loop fasteners. The second embodiment is especially well adapted for use in incubators constructed to move neonatal patients from one medical facility to another. When used for this purpose the likelihood that the releasable fastener assemblies are accidentally released is significantly limited because the infant and patient restraint are typically transported within an incubator and therefore the releasable fastener assemblies are not likely to be accidently bumped or hit. Therefore, the use of hook and loop fasteners is acceptable for the second embodiment of the patient restraint 210. In the alternative, however, the other releasable fastener assemblies described for the first embodiment may be used.

Note that the padding used for the straps may be in the form of a soft loop portion of a hook and loop fastener. Thereby the padding will act not only as a protection for the infant's delicate skin, but also as one half of a hook and loop fastener used for fastening transverse strap, 220 and 222, and shoulder straps, 80 and 82.

The second embodiment of the patient restraint 210 is attached to the isolet 16 by extending the second connectors 234 downward through one of the apertures 18 in the isolet 16 and then upward around the edge of the isolet. The second connectors 234 (one half of a hook and loop fastener) are then fastened to the first connectors 230 (the opposing half of a hook and loop fastener), thereby fastening the patient restraint 210 to the isolet 16. The effective length of the transverse straps, 220 and 222, can be adjusted by changing the location of the second connectors 234 on the first connectors 230 along the length of the transverse straps, 220 and 222, thereby tightening or loosening the patient restraint 210 against the body of the patient.

Figure 7:
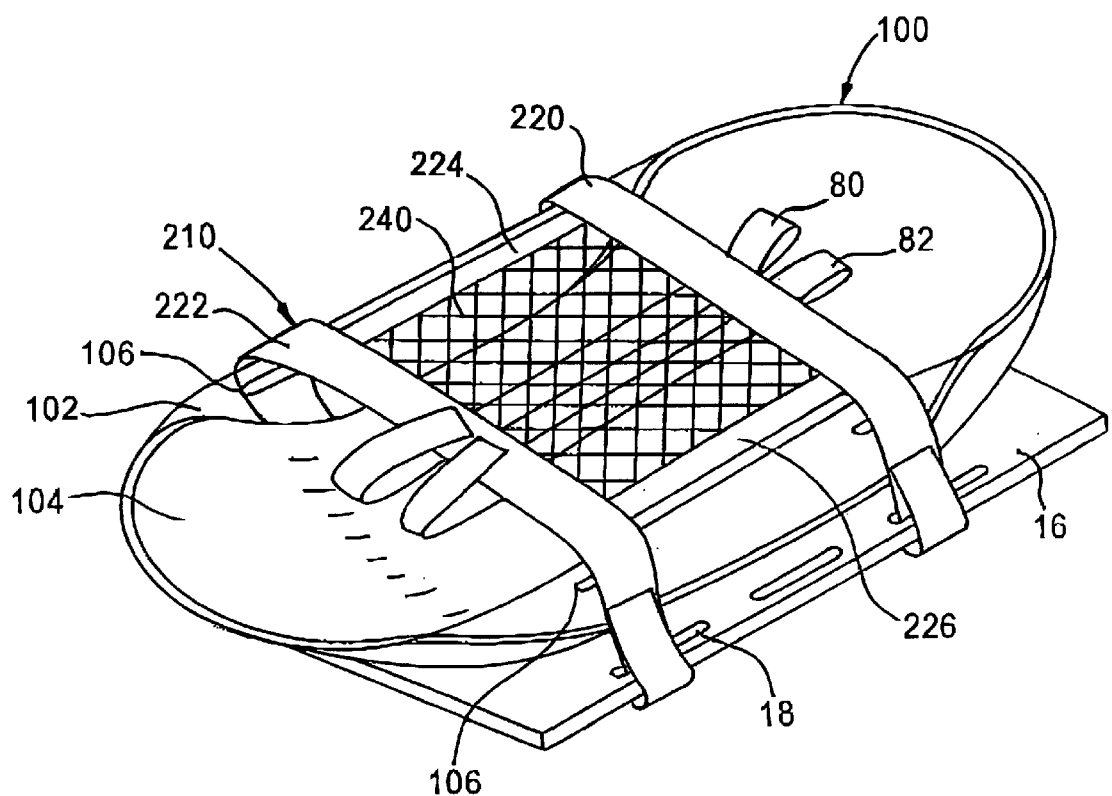
FIG. 7 is a perspective view of a second embodiment of a patient restraint used in conjunction with a supporting structure such as a transport cradle and/or an isolet.

FIG. 7 is a perspective view of the second embodiment of a patient restraint 210 used in conjunction with supporting structures such as a transport cradle 100 and an isolet 16. The transport cradle 100 is preferably manufactured to form a shell 102 which is lined with cushioning 104 to protect the infant. Preferably, the shell is made from transparent plastic, as shown in FIG. 7, although other similar materials may alternatively be used. Plastic is preferred because it is easy to clean, sanitize, and maintain. The cushioning 104 is attached to the interior of the shell 102.

The transport cradle 100 is used in conjunction with the patient restraint 210 by attaching the releasable fastener assemblies of the patient restraint to the apertures 18 in the isolet 16 as depicted in FIG. 7. Alternatively, the transverse straps, 220 and 222, may be looped under and around the shell 102 and the second connectors 234 attached to either first connectors 230 on their respective transverse straps. Additionally, apertures 106 may be formed in the sides of the cradle shell 102 and the releasable fastener assemblies used to secure the patient restraint 210 to the apertures 106. The transverse straps, 220 and 222, may also be threaded through the apertures 106 in the shell and then the releasable fastener assemblies can be used to secure the patient restraint 210 and the cradle 100 to the apertures 18 in the isolet 16. The transport cradle 100 may also include conventional restraining devices (not shown) within the cradle 100 to restrain the infant. These restraining devices may be a simple hook and loop fastener style seatbelt, i.e. two straps each having one end attached to the cradle and one free end with a hook and loop fastener, or they can be similar in construction to automobile safety seat restraint devices.

The above invention, including both the first and the second embodiments, can be used to aid hospital workers and emergency personnel in administering treatment to a variety of patients. For example, the patient restraint of the present invention can be used to immobilize a patient while the patient is receiving sutures or while the patient is being examined. The patient restraint can also be used to immobilize a patient while the patient is being x-rayed. The patient restraint can prevent an unattended and incapacitated emergency room patient from accidentally rolling off a gurney or out of bed. The patient restraint of the present invention clearly has numerous applications in the field of medicine and can be used for all sizes and ages of patients.

It will be readily seen by one of ordinary skill in the art that the present invention fulfills all the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

What is claimed is:

1. A patient restraint device for releasable attachment to a patient supporting structure, said patient restraint device comprising:

a first elongated member;

a second elongated member;

a net interconnected between said first elongated member and said second elongated member, wherein said net is an open lattice network enabling visual inspection of wounds on a patient restrained by said patient restraint device to the supporting structure, or enabling administration of medical attention to the patient;

a first releasable fastener assembly attached to said first elongated member for attachment of said first elongated member to a first side of the patient supporting structure;

a second releasable fastener assembly attached to said first elongated member for attachment of said first elongated member to a second side of the patient supporting structure;

a third releasable fastener assembly attached to said second elongated member for attachment of said second elongated member to the first side of the patient supporting structure; and a fourth releasable fastener assembly attached to said second elongated member for attachment of said second elongated member to the second side of the patient supporting structure.

2. The patient restraint device of claim 1 wherein:

said first elongated member has a first terminal end; and said first releasable fastener assembly comprises:

a first connector attached to said first elongated member, and a second connector attached to said first terminal end of said first elongated member, whereby a portion of said first elongated member between said first connector and said second connector extends around a portion of the patient supporting structure, and said first connector is adapted to releasably mate with said second connector to form a closed loop attaching said first releasable fastener assembly to the patient supporting structure.

3. The patient restraint device of claim 1 wherein said first and said second elongated straps each have first and second terminal ends, said first and said second terminal ends of said first and said second elongated straps extending beyond said net.

4. The patient restraint device of claim 1 wherein said net is sized according to a type of patient to be restrained by said patient restraint device, whereby the patient is in continuous contact with said net and whereby the patient is restrained between said patient restraint device and the supporting structure.

5. The patient restraint device of claim 4 wherein the type of patient is an infant, a child, or an adult.

6. The patient restraint device of claim 1 further comprising:
 a third elongated member connected between said first elongated member and said second elongated member, said net being connected to said third elongated member; and
 a fourth elongated member connected between said first elongated member and said second elongated member, said net being connected to said fourth elongated member.

7. The patient restraint device of claim 6 wherein said first releasable fastener assembly comprises a first connector attached to said first elongated member at a position adjacent to a position where said first elongated member is connected to said third elongated member and a second connector attached to a terminal end of said first elongated member, said first connector and said second connector being adapted to releasably mate.

8. The patient restraint device of claim 6 wherein said net has a periphery, said periphery of said net being connected to said first elongated member, said second elongated member, said third elongated member, and said fourth elongated member.

9. The patient restraint device of claim 1 wherein said first releasable fastener assembly is a side release fastener, a releasable buckle, or a hook and loop fastener.

10. The patient restraint device of claim 1 further comprising:
 a fifth elongated member having a fixed end connected to said first elongated member near a center of said first elongated member and a free end, said free end being releasably fastened to said second elongated member, said fifth elongated member forming respectively first and second patient restraining loops proximate said first and second elongated members when said free end of said fifth elongated member is fastened to said second elongated member; and
 a sixth elongated member having a fixed end connected to said first elongated member near a center of said first elongated member and a free end, said free end being releasably fastened to said second elongated member, said sixth elongated member forming respectively first and second patient restraining loops proximate said first and second elongated members when said free end of said sixth elongated member is fastened to said second elongated member.

11. The patient restraint device of claim 10 wherein said first elongated member, said second elongated member, said fifth elongated member, and said sixth elongated member have padding thereon.

12. The patient restraint device of claim 1 wherein said first elongated member is a strap.

13. The patient restraint device of claim 1, wherein said net is a single layer open lattice network of unitary construction.

14. A patient restraint assembly comprising:
 a patient supporting structure having a first side and a second side; and
 a patient restraint device for releasable attachment to said patient supporting structure, said patient restraint device comprising:
  a first elongated member,
  a second elongated member,
  a net interconnected between said first elongated member and said second elongated member, wherein said net is an open lattice network enabling visual inspection of wounds on a patient restrained by said patient restraint device to said supporting structure, or enabling administration of medical attention to the patient,
  a first releasable fastener assembly attached to said first elongated member for attachment of said first elongated member to said first side of said patient supporting structure,
  a second releasable fastener assembly attached to said first elongated member for attachment of said first elongated member to said second side of said patient supporting structure,
  a third releasable fastener assembly attached to said second elongated member for attachment of said second elongated member to said first side of said patient supporting structure, and
  a fourth releasable fastener assembly attached to said second elongated member for attachment of said second elongated member to said second side of said patient supporting structure.

15. The patient restraint assembly of claim 14 wherein:
 said first elongated member has a first terminal end; and
 said first releasable fastener assembly comprises:
  a first connector attached to said first elongated member, and
  a second connector attached to said first terminal end of said first elongated member, whereby a portion of said first elongated member between said first connector and said second connector extends around a portion of said patient supporting structure, and said first connector is adapted to releasably mate with said second connector to form a closed loop attaching said first releasable fastener assembly to said patient supporting structure.

16. The patient restraint assembly of claim 14 wherein said patient supporting structure comprises a transport member having a riser portion attached to a bottom surface of said transport member.

17. The patient restraint assembly of claim 16 wherein said transport member has a plurality of apertures extending along two opposing edges of said transport member, said plurality of apertures being arranged in two parallel rows along each of said two opposing edges of said transport member.

18. The patient restraint assembly of claim 14 wherein said patient supporting structure comprises a transport cradle having a concave interior surface defining a receptacle sized to safely retain an infant in the cradle, said interior surface having a cushion member attached thereto.

19. The patient restraint assembly of claim 18 wherein said transport cradle has a plurality of apertures extending along two opposing edges of said transport cradle.

20. The patient restraint assembly of claim 14 wherein said patient supporting structure is made of a plastic material.

21. A patient restraint device for releasable attachment to a patient support structure, said patient restraint device comprising:
- a first elongated member;
- a second elongated member;
- a net interconnected between said first elongated member and said second elongated member, wherein said net is an open lattice network enabling visual inspection of wounds on a patient restrained by said patient restraint device to the supporting structure, or enabling administration of medical attention to the patient;
- a first releasable fastener assembly attached to said first elongated member for attachment of said first elongated member to the patient supporting structure; and
- a second releasable fastener assembly attached to said second elongated member for attachment of said second elongated member to the patient supporting structure, wherein
  said first elongated member has a first terminal end; and
  said first releasable fastener assembly comprises:
    - a first connector attached to said first elongated member, and
    - a second connector attached to said first terminal end of said first elongated member, whereby a portion of said first elongated member between said first connector and said second connector extends around a portion of the patient supporting structure, and said first connector is adapted to releasably mate with said second connector to form a closed loop attaching said first releasable fastener assembly to the patient supporting structure.

22. The patient restraint device of claim 21 wherein said first and said second elongated straps each have first and second terminal ends, said first and said second terminal ends of said first and said second elongated straps extending beyond said net.

23. The patient restraint device of claim 22 further comprising:
- a third elongated member connected between said first elongated member and said second elongated member, said net being connected to said third elongated member; and
- a fourth elongated member connected between said first elongated member and said second elongated member, said net being connected to said fourth elongated member.

24. The patient restraint device of claim 23 wherein said first releasable fastener assembly comprises a first connector attached to said first elongated member at a position adjacent to a position where said first elongated member is connected to said third elongated member and a second connector attached to a terminal end of said first elongated member, said first connector and said second connector being adapted to releasably mate.

25. The patient restraint device of claim 22 further comprising:
- a fifth elongated member having a fixed end connected to said first elongated member near a center of said first elongated member and a free end, said free end being releasably fastened to said second elongated member, said fifth elongated member forming respectively first and second patient restraining loops proximate said first and second elongated members when said free end of said fifth elongated member is fastened to said second elongated member; and
- a sixth elongated member having a fixed end connected to said first elongated member near a center of said first elongated member and a free end, said free end being releasably fastened to said second elongated member, said sixth elongated member forming respectively first and second patient restraining loops proximate said first and second elongated members when said free end of said sixth elongated member is fastened to said second elongated member.

* * * * *